United States Patent
Meyer

(10) Patent No.: US 7,231,013 B2
(45) Date of Patent: Jun. 12, 2007

(54) PRECISE X-RAY INSPECTION SYSTEM UTILIZING MULTIPLE LINEAR SENSORS

(75) Inventor: Gerald L Meyer, Ft Collins, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 156 days.

(21) Appl. No.: 10/394,632

(22) Filed: Mar. 21, 2003

(65) Prior Publication Data

US 2004/0184576 A1 Sep. 23, 2004

(51) Int. Cl.
*G01N 23/02* (2006.01)
(52) U.S. Cl. .......................... 378/58; 378/22
(58) Field of Classification Search ............... 378/58, 378/21–27, 57, 2; 250/358.1–360.1
See application file for complete search history.

(56) References Cited

U.S. PATENT DOCUMENTS

| | | | |
|---|---|---|---|
| 4,609,823 A * | 9/1986 | Berger et al. | 250/370.09 |
| 4,926,452 A | 5/1990 | Baker et al. | |
| 5,020,086 A | 5/1991 | Peugeot | |
| 5,500,886 A | 3/1996 | Duff | |
| 5,541,856 A | 7/1996 | Hammermeister | |
| 5,583,904 A * | 12/1996 | Adams | 378/22 |
| RE35,423 E | 1/1997 | Adams et al. | |
| 5,594,768 A * | 1/1997 | Fujii et al. | 378/21 |
| 5,594,770 A | 1/1997 | Bowles et al. | |
| 6,324,249 B1 | 11/2001 | Fazzio | |
| 6,584,170 B2 * | 6/2003 | Aust et al. | 378/57 |
| 6,591,003 B2 * | 7/2003 | Chu et al. | 382/133 |
| 6,628,746 B2 * | 9/2003 | Eppler et al. | 378/21 |
| 6,853,707 B2 * | 2/2005 | Kerschner | 378/98.8 |
| 6,891,179 B2 * | 5/2005 | Batten et al. | 250/515.1 |
| 6,904,122 B2 * | 6/2005 | Swift et al. | 378/41 |
| 2003/0174806 A1 | 9/2003 | Francke et al. | |

* cited by examiner

*Primary Examiner*—Edward J. Glick
*Assistant Examiner*—Chih-Cheng Glen Kao
(74) *Attorney, Agent, or Firm*—Anil N. Balchandani

(57) ABSTRACT

An x-ray inspection is provided featuring a single x-ray source and a planar array of linear sensors aligned in parallel. An article to be inspected is moved between the x-ray source and the linear sensors in a series of passes parallel to the array of linear sensors and substantially perpendicular to the long axes of the linear sensors. Alternately, the x-ray source and the sensors are moved as a unit relative to a stationary article. As a result, a transmission image of the article is captured for each of the linear sensors. These transmission images are then combined mathematically to generate a layer image for each separate conceptual layer of the article. In some embodiments, these layer images may then be interpreted in order to determine the quality of the article.

27 Claims, 5 Drawing Sheets

PRECISE X-RAY INSPECTION SYSTEM UTILIZING MULTIPLE LINEAR SENSORS

BACKGROUND OF THE INVENTION

For some years now, three-dimensional (3-D) x-ray inspection systems have been a popular alternative to previously available physical inspection and diagnosis technologies: Such systems are now commonly used for defect analysis and quality inspection of manufactured articles, such as electronic printed circuit boards (PCBs). The use of these systems allows rather detailed inspection of areas of an article that are either too small to be seen with the naked eye, or are obscured from direct view.

Several types of 3-D x-ray inspection systems are now available, each with their own inherent advantages and limitations. For example, x-ray laminography systems, such as the one described in U.S. Pat. No. 4,926,452 by Baker et al., utilize an angled, rotating x-ray source in conjunction with a moving area image detector to acquire an image of a single planar layer of an article under inspection. Due to the rotational movement of the source and the image area detector, the layer of concern within an area under inspection is viewed from a continuous range of oblique viewpoints so that other layers of the article do not remain stationary within the area of view. This movement essentially causes those other layers to fade from the resulting image. The result is that only those features within the layer that reside in the "focal plane" described by the rotating x-ray source and detector are prominent.

While x-ray laminography systems are exceptionally useful in many applications, such systems require rather expensive and complex technology, including the x-ray tube and drive electronics needed to implement the precise movements of an electron beam within the tube used to generate the rotating source of x-rays. Also, the movement of the area image detector must be accurately coordinated with the motion of the x-ray source. Precise mechanics and electronics for moving the article under examination both horizontally and vertically are typically necessary so that both the area and the layer of the article to be inspected lie within the system focal plane. Furthermore, due to the rather small areas such systems are capable of inspecting at any one time, the number of areas and layers that are normally required to fully inspect an article are typically rather large. As a result, such a system may require a rather protracted amount of time to perform a complete examination of each article. Additionally, laminography systems normally require the execution of a preliminary process called "surface mapping" for each article to be inspected. This mapping essentially measures the height of numerous locations on the surface of the article under inspection so that proper positioning of the article within the system focal place for each small inspection area may be accomplished.

Another category of x-ray inspection systems similarly involves the use of a moving x-ray source. However, instead of generating a continuous moving image during a rotation of the source, two or more discrete images are generated by way of a single large stationary image intensifier or several smaller stationary area image sensors. Such systems, examples of which are described by Adams et al. in U.S. Pat. No. Re. 35,423 and by Peugeot in U.S. Pat. No. 5,020,086, allow the x-ray source to dwell at particular angles through the area of interest on the article. The resulting discrete image at each beam orientation is then stored digitally. All of the images for a particular area and layer of the article under inspection are then mathematically processed by way of either computer hardware or software so that a single image representing the area and layer under inspection may be generated. Such inspection systems eliminate the need for precise coordination of image sensor movement with that of the x-ray source. However, the moving image sensor is replaced by multiple, expensive x-ray area image sensors, or in the alternative by a large image intensifier that normally exhibits reduced resolution and increased geometric distortion at a possibly higher cost.

An alternate x-ray inspection system, as discussed in U.S. Pat. No. 5,583,904 issued to Adams, uses one or two x-ray tubes in conjunction with two to four linear x-ray image sensors. The x-ray sources of the tubes do not rotate, but require the use of collimators and shields to guide the x-rays appropriately onto the image sensors. The article to be inspected is then transported horizontally across the linear sensors, each of which must be long enough to allow an image across the entire width of the article in a single pass. This requirement thus results in either a limit on the size of articles to be inspected, or in higher costs resulting from the use of exceptionally long linear sensors. As the board passes by the sensors, each sensor acquires a series of sequential linear images which are subsequently stored for later computer processing to generate an image for each layer of the article. While such a system decreases the total amount of inspection time for a particular article by limiting the movement of the board to a single linear pass across the sensors, the number and variety of angles that can be implemented to capture quality images of the article layers are severely limited. Additionally, the use of two x-ray tubes complicates the overall design because of the additional collimating and shielding that is necessary to prevent x-rays from two separate tubes from illuminating the same linear sensor.

From the foregoing, although several different methods of implementing an x-ray inspection system exist, with each exhibiting its own level of complexity, cost, speed and image quality, a need still exists for an x-ray inspection system that provides accurate, detailed images of the various layers of an article under inspection while significantly reducing overall inspection time and system cost.

SUMMARY OF THE INVENTION

Embodiments of the invention, to be discussed in detail below, provide an x-ray inspection system that utilizes an imaging chain comprising a single x-ray source and a planar array of linear sensors, with the x-ray source and the linear sensors remaining stationary in relation to each other. The long axes of the linear sensors are aligned in parallel. Each of the linear sensors is positioned to receive x-rays from the x-ray source. A relative motion mechanism is employed to move an article under inspection between the x-ray source and the array of linear sensors in a series of passes that are parallel to the sensor array and substantially perpendicular to the long axes of the sensors. Alternately, the x-ray source and the array of linear sensors may be moved as a unit in relation to a stationary article under inspection. An interpreter captures a transmission image of the article for each of the linear sensors. These images are then combined to generate a layer image for each conceptual "layer" of the article. The layer images may then be interpreted to determine the overall quality of the article, including the possible presence of unacceptable faults or defects. A controller, such as computer, for example, coordinates and controls the imaging chain, the relative motion mechanism, and the interpreter.

The use of a single x-ray source, which requires no electron beam steering or collimating due to the stationary nature of the source in relation to sensors, greatly simplifies the design of the system. Also, the utilization of multiple linear sensors that are stationary with respect to the x-ray source reduces system cost and complexity while producing the varied view angles required for thorough inspection of an article.

Other aspects and advantages of the invention will become apparent from the following detailed description, taken in conjunction with the accompanying drawings, illustrating by way of example the principles of the invention.

DETAILED DESCRIPTION OF THE PREFERRED EMBODIMENTS

Figure 1:
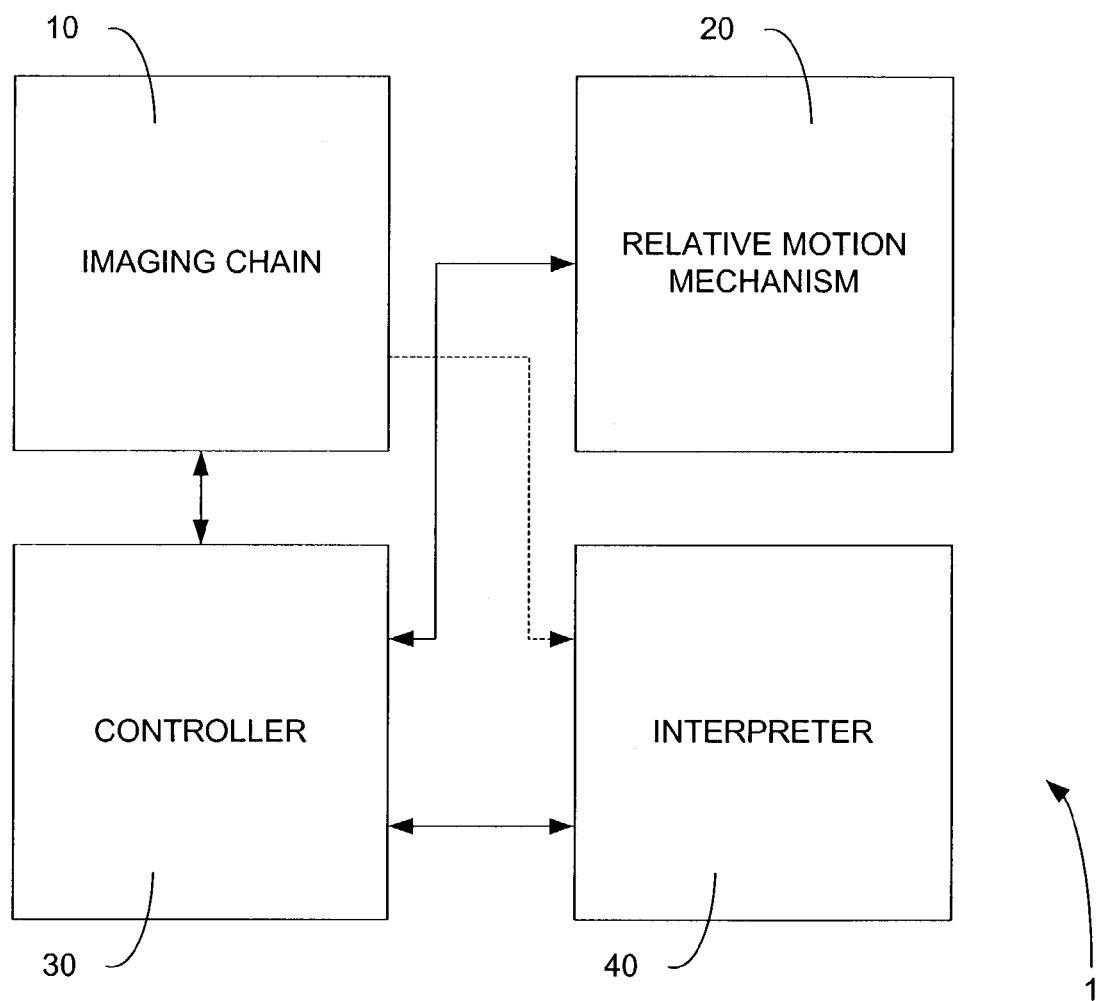
FIG. 1 is a block diagram of an x-ray inspection system according to an embodiment of the invention.

An example of an x-ray inspection system 1 according to an embodiment of the invention is shown in FIG. 1. An imaging chain 10 is employed to obtain x-ray images of an article under inspection. In this particular embodiment, the article is an electronic printed circuit board (PCB). In other embodiments, any article of manufacture susceptible to inspection by the use of x-rays may be inspected by such a system. A relative motion mechanism 20 is used to maneuver the article under inspection in relation to the imaging chain 10 so that various areas of the article may be inspected. In other embodiments, the relative motion mechanism 20 moves the imaging chain 10 in relation to a stationary article. An interpreter 40 then takes the x-ray images as input to generate a series of layer images, each exposing a separate conceptual "layer" of the article. The interpreter 40 may then process such images in order to ascertain the overall quality of the article under inspection by comparing the resulting layer images with a preexisting database that the interpreter 40 uses as a comparative model. For example, algorithmic image processing of the layer images may be performed on areas of particular interest of the PCB to determine the structural integrity and reliability of solder joints. A controller 30 is utilized to coordinate the actions of the imaging chain 10, the relative motion mechanism 20, and the interpreter 40. The controller 30 may also be used to facilitate the transfer of image data between the imaging chain 10 and the interpreter 40, although some embodiments may allow image data transfer directly from the imaging chain 10 to the interpreter 40.

Figure 2:
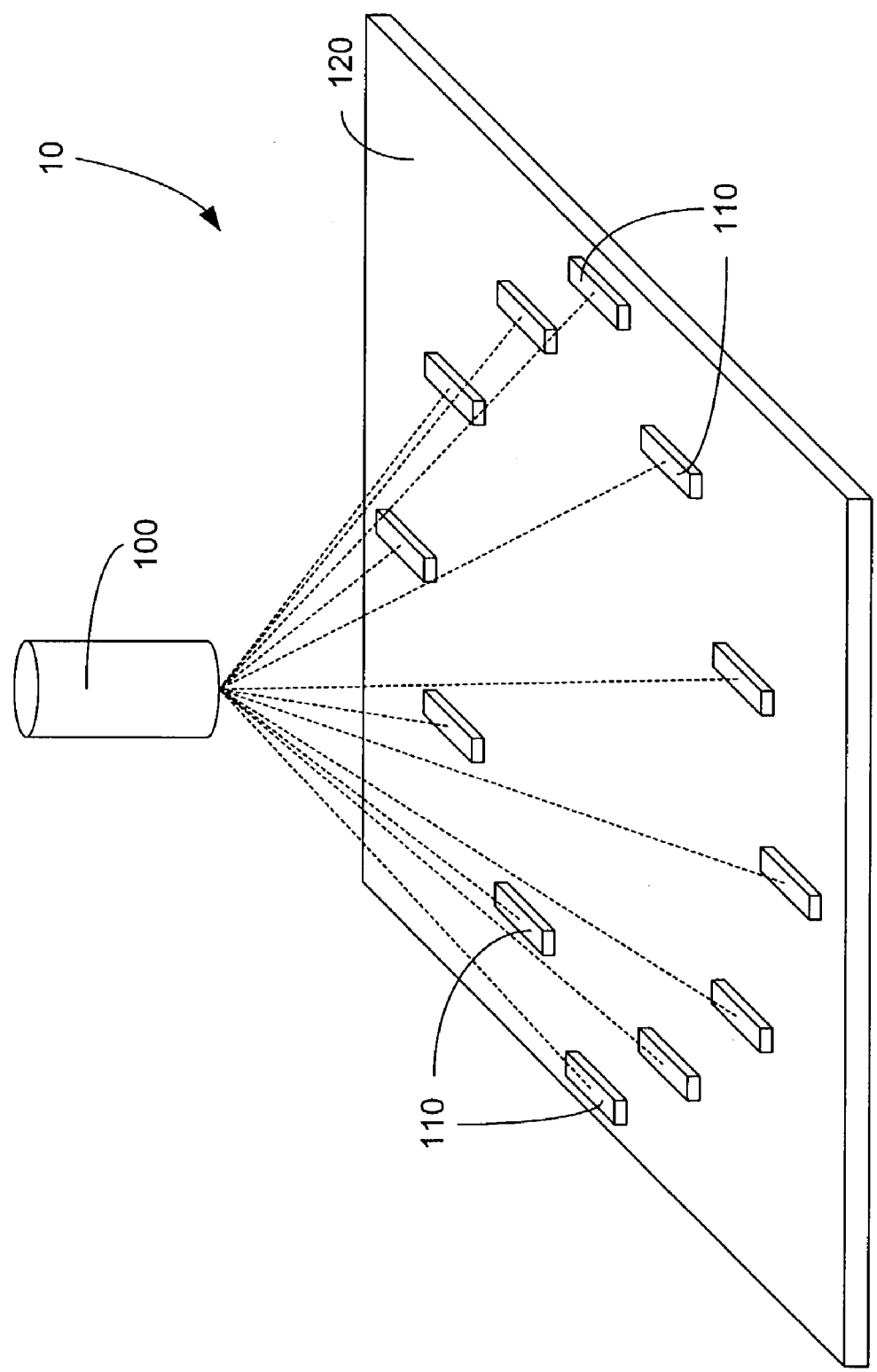
FIG. 2 is a perspective view of the imaging chain of an x-ray inspection system according to an embodiment of the invention.

The imaging chain 10 is shown in greater detail in FIG. 2. A single x-ray source 100, such as that generated by a simple x-ray tube, is employed to irradiate a planar array of linear sensors 110 that are sensitive to x-rays. Unlike the x-ray source of a typical x-ray laminography system, which normally requires specialized drive electronics to move an electron beam within an x-ray tube to facilitate movement of the x-ray source, no such electronics are required in embodiments of the present invention. The x-ray source 100 remains stationary relative to the array of linear sensors 110, projecting x-rays toward all of the linear sensors 110 simultaneously. Furthermore, collimation of the x-rays from the x-ray source 100 is not required to prevent x-rays generated from multiple sources illuminating a particular sensor since only a single source is implemented. However, collimation in some embodiments may be employed to merely restrict x-ray exposure to the locations occupied by the linear sensors 110 and the intervening areas of the article under inspection in order to limit overall x-ray exposure of the article.

An article to be inspected (not shown in FIG. 2) is positioned between the x-ray source 100 and the linear sensors 110 so that each of the sensors 110 may capture images of the article after the x-rays have transmitted through the article. Each of the linear sensors 110 are positioned relative to the x-ray source 100 so that the transmission image of the article captured by each sensor 110 is acquired at a distinct angle relative to the x-ray source 100. In the example of FIG. 2, a total of twelve linear sensors 110 are arranged in a circular configuration, resulting in a difference in viewing angle between adjacent linear sensors 110 of approximately 30 degrees. While any number of linear sensors may be employed to generate different viewing angles of the article under inspection, a range of twelve to sixteen linear sensors 110 appears to generate a sufficient number of images for proper inspection of PCBs. An implementation of eight linear sensors would probably be considered a practical minimum for most inspection applications. In many cases, the use of more than sixteen linear sensors 110 does not add significantly to the inspection capabilities of the system 1 to justify the costs involved in employing the additional sensors. Also, while a circular configuration is implemented in the example of FIG. 2, any number of different sensor arrangements, such as those defining a square, diamond, or a more randomized pattern, may be utilized, as long as the long axes of the linear sensors 110 are aligned essentially in parallel. Depending on the application, the configuration selection may be based to some extent on the ease of implementation of the selected configuration, and the desired image quality of the type of articles to be inspected.

Each of the linear sensors 110 is stationary relative to each other and to the x-ray source 100 by way of attachment to a stable base, such as a system circuit board 120, as shown in FIG. 2. The stationary nature of the sensors is unlike that of typical x-ray laminography systems of the prior art, which often require a synchronized circular movement of an area sensor in conjunction with a moving x-ray beam. As a result, the overall cost of the system 1 relative to those of most prior-art x-ray inspection systems is greatly reduced. Also, linear sensors tend to be far less expensive than area sensors due to the reduced number of imaging pixels employed and the mature nature of linear sensor technology, thus making the system 1 even more cost-effective.

The linear sensors 110, in some embodiments, are standard linear sensors, each having a single row of several hundred to a few thousand imaging pixels, which are adapted to be sensitive to the x-rays from the x-ray source 100. For example, the linear sensors 110 may be commercially available 300 dot-per-inch (DPI) or 600 DPI chargecoupled device (CCD) sensors mounted with a fiber optic plate (FOP) and a cesium-iodide x-ray scintillator. Periodically, voltages denoting the intensity level detected by each pixel typically are transferred to a shift register that is read by the controller 30 or the interpreter 40 of the system 1, normally via an analog-to-digital converter (ADC). Alternately, the linear sensors 110 may be time delay integration (TDI) linear sensors, which employ multiple rows of sensors to integrate the charge generated as a result of the received x-rays before being converted to a voltage. TDI linear sensors are known in the art for their excellent sensitivity and applicability in high-speed imaging applications. Other linear sensors that are sensitive to x-rays may also be employed in the system 1, depending on the technical requirements of the application involved.

Figure 3:
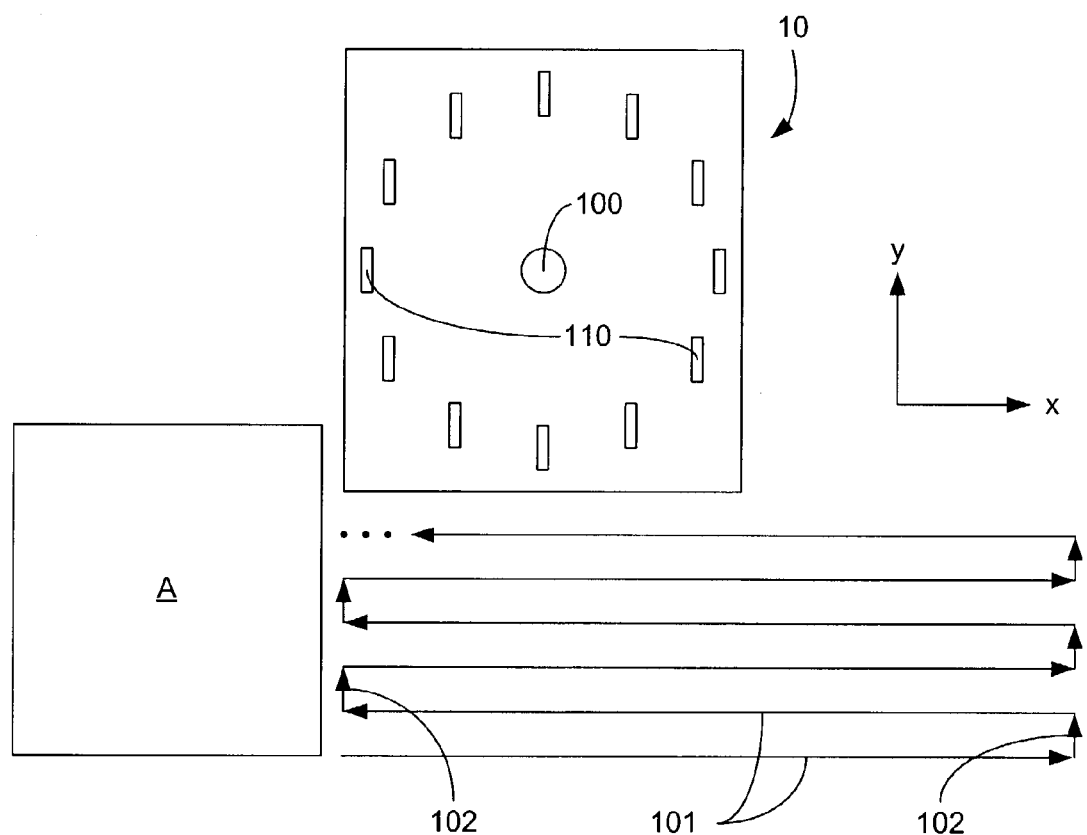
FIG. 3 is a plan view diagram describing the motion of an article under inspection in relation to the imaging chain of an x-ray inspection system according to an embodiment of the invention.

To capture images of all areas of interest of the article under inspection, the relative motion mechanism 20 moves the article between the x-ray source 100 and the array of linear sensors 110 in a series of passes over the sensors substantially perpendicular to the long axis of each sensor. For example, FIG. 3 displays a PCB A that is to be inspected for defects, such as solder bridges, circuit trace breaks, and the like. As shown by the directional arrows in FIG. 3, the relative motion mechanism 20 causes the board A to make a horizontal pass 101 over the linear sensors 110 and under the x-ray source 100 in the x-direction perpendicular to the y-axis-aligned sensors 110. As this horizontal pass 101 occurs, each sensor 110 that is located under the board A captures multiple linear images of a portion of the board A. By the time the horizontal pass is complete, a portion of a transmission image having the width of the board A and the length of a sensor 110 (maximum) has been captured by each sensor under the board A. Once the board A has passed beyond the array of sensors, the board then makes a vertical advancement 102 in the y-direction by approximately the length of view for each linear sensor 110. The relative motion mechanism 20 then moves the board A in the negative x-direction by way of another horizontal pass 101, during which time each sensor 110 captures another swath of the board A. The motion of the board progresses in this manner until each linear sensor 110 has captured a transmission image of the entire board A, or at least the entire area to be inspected. As can be seen in FIG. 3, due to the diverse locations of the various sensors, each sensor likely has collected a different amount of the overall image of the board A at any particular moment while the board A is being transported by the relative motion mechanism 20. However, by the time the board A has passed over every sensor 110, a complete transmission image for each sensor 110 has been collected.

While the most advantageous embodiments of the present invention likely utilize a relative movement of the article under inspection perpendicular to the long axis of the linear sensors 110, other embodiments may implement a relative motion slightly askew (e.g., by 10 degrees or so) of a strictly perpendicular motion. Such relative motion would cause a minor non-orthogonal appearance to the resulting transmission images, but that distortion could be compensated for by the interpreter 40 when the layer images are generated from the transmission images. However, use of a relative motion that is as close to perpendicular as is practical essentially eliminates the need for the interpreter 40 to compensate for such distortion.

Figure 4:
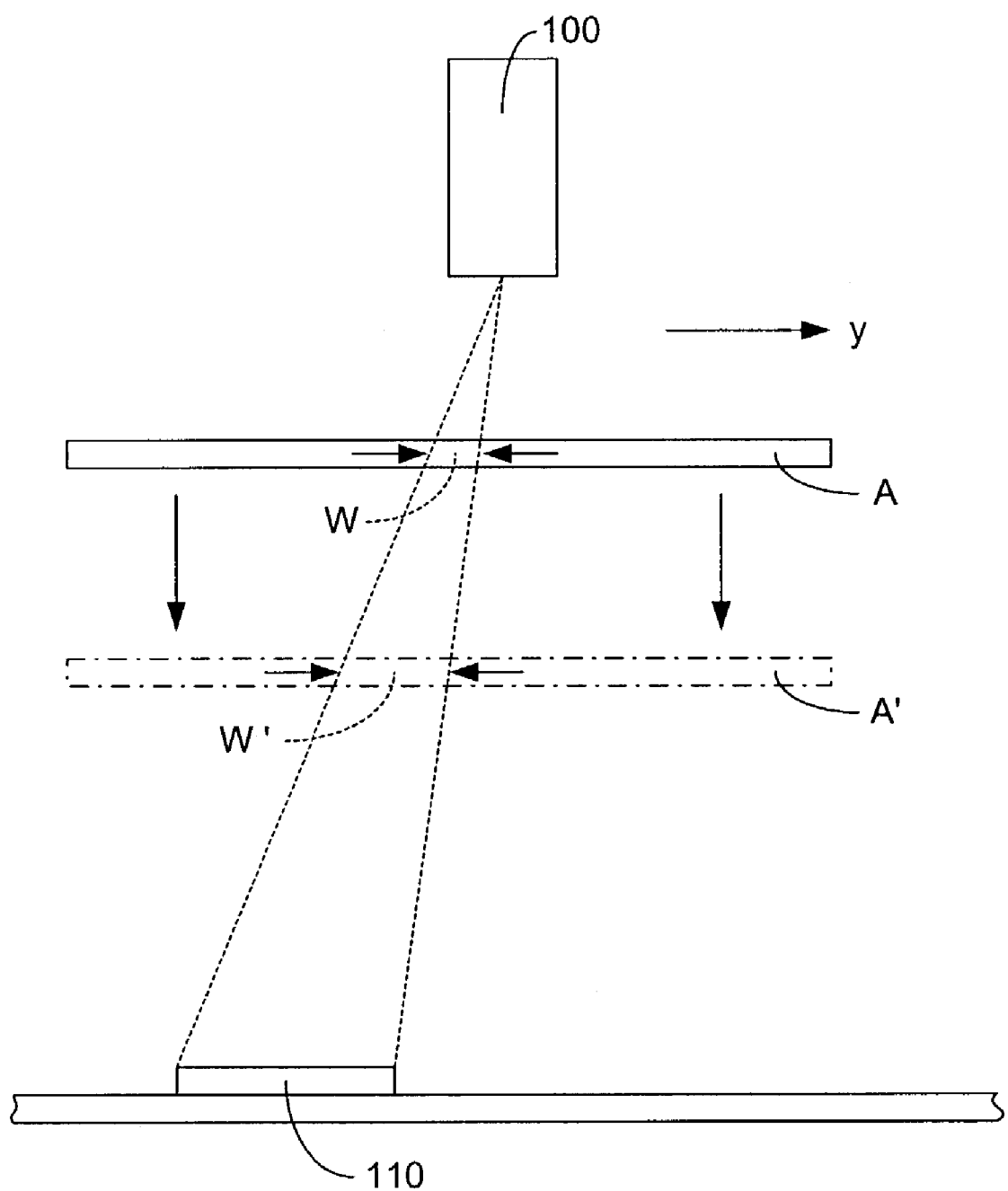
FIG. 4 is a side view diagram indicating the effect of altering the relative position of an article under inspection in relation to the imaging chain of an x-ray inspection system according to an embodiment of the invention.

As noted above, the length of each vertical advancement 102 of the board is essentially the length of view for each sensor, which in turn is related to the actual length of each sensor. In FIG. 4, a swath of width W of board A is projected onto one of the linear sensors 110 by way of the x-rays emitted from the x-ray source 100. Thus, in the case of FIG. 4, each vertical advancement 102 of the board A would be approximately the width W so that no areas of the board A are missed, while at the same time no significant overlap of the separate swaths of the board A taken by each horizontal pass 101 occurs.

In alternate embodiments, each linear sensor 110 may be conceptually divided into two or more "logical sensors," with each logical sensor being situated at a distinct angle from the x-ray source 100, thus providing yet more transmission images representing different viewing angles. In such embodiments, each vertical advancement 102 of the board A would then correspond with a fraction of the length of view for each logical sensor. In the example of FIG. 4, assuming each linear sensor 110 is subdivided into two logical sensors, each vertical advancement 102 of the board A would be approximately width W/2 in order to ensure that each logical sensor was employed to image the entire area of interest of the board A.

Since the x-ray source 100 and the linear sensors 110 are all stationary with respect to each other, no "focal plane" is associated with the generation and subsequent manipulation of the transmission images, unlike x-ray laminography systems. As a result, no surface mapping of the article under inspection is required in order to account for warping or other irregularities of the article, and no vertical or rotational adjustment of the article by way of relative motion mechanism 20 is required.

However, in alternate embodiments, one advantage of maintaining a vertical movement capability for the relative motion mechanism 20 would be to vary the image resolution of the system 1. In looking again at FIG. 4, referenced above, an alternate vertical position for board A, indicated as A', is displayed which is closer to the linear sensors 110. This position results in a wider swath W' being imaged for each horizontal pass 101 of the board A'. Therefore, fewer horizontal passes W' are required to capture the multiple transmission images of the entire board A', resulting in a faster imaging process. However, since the number of imaging pixels remains constant, the wider swath W' results in a lower image resolution compared to the position of board A. In other words, a tradeoff between resolution and processing speed would be made available as a result of a positioning capability of the relative motion mechanism 20 that could alter the vertical position of the article under inspection relative to the x-ray source 100 and the linear sensors 110.

As, can be seen from the foregoing discussion, the length of each of the linear sensors 110 is not related directly to the size of the article under inspection, as any number of multiple horizontal passes 101 may be made to create transmission images of the entire article. Thus, no substantive limit exists on the size of the article under inspection relative to the size of the linear sensors 110 used, thus allowing relatively small and inexpensive sensors to be employed in the design of the system 1.

The relative motion mechanism 20 represents a simplified movement structure than those required for many other x-ray inspection systems. The movement of the article under inspection is essentially at a constant velocity during each of the horizontal passes 101, so a mechanism requiring fast article acceleration and short settling times is not necessary. Furthermore, all changes of direction (between the x and y directions) occur while no imaging is being performed, so lower performance mechanics with respect to changes of direction may be tolerated. The relative motion mechanism 20 may typically consist primarily of a set of inexpensive stepper motors under the direction of the controller 30, although other motor technologies, such as direct current (DC) servo motors, may also be employed. Alternately, the relative motion mechanism 20 may instead move the x-ray source 100 and the linear sensors 110 in relation to a stationary article under inspection in a manner as described above; such a system may be preferable for large bulky articles.

Once a transmission image of at least some portion of the article under inspection is acquired for each linear sensor 110, the interpreter 40 uses mathematical processes known in the art to transform the single set of transmission images into a set of layer images, whereby each layer image is a representation of the structural makeup of a conceptual "layer" of the article under inspection. Typically, this transformation consists in part of an averaging process across each of the transmission images to emphasize physical characteristics of each conceptual layer of the article. The transformation process may begin as soon as transmission images from each of the sensors have been captured for a particular area of the article. One such possible process for converting the transmission images into layer images is described by Adams in U.S. Pat. No. 5,583,904, entitled "CONTINUOUS LINEAR SCAN AND LAMINOGRAPHY SYSTEM AND METHOD". Alternate methods for performing essential the same function may also be employed.

After the layer images are generated, the interpreter 40 may then utilize the layer images to determine the overall quality of the article under inspection. For example, in the case of an electronic printed circuit board, features of each layer, such as printed wires, vias, solder joints, and the like, can be compared automatically to a preexisting set of images or structural measurements to ascertain the physical quality of the PCB. The preexisting set of images or measurements may be generated by way of a theoretical standard or a known good PCB. Furthermore, image processing algorithms known in the art may be employed to process key portions of the layer images to determine overall quality and other desired parameters of those portions.

Figure 5:
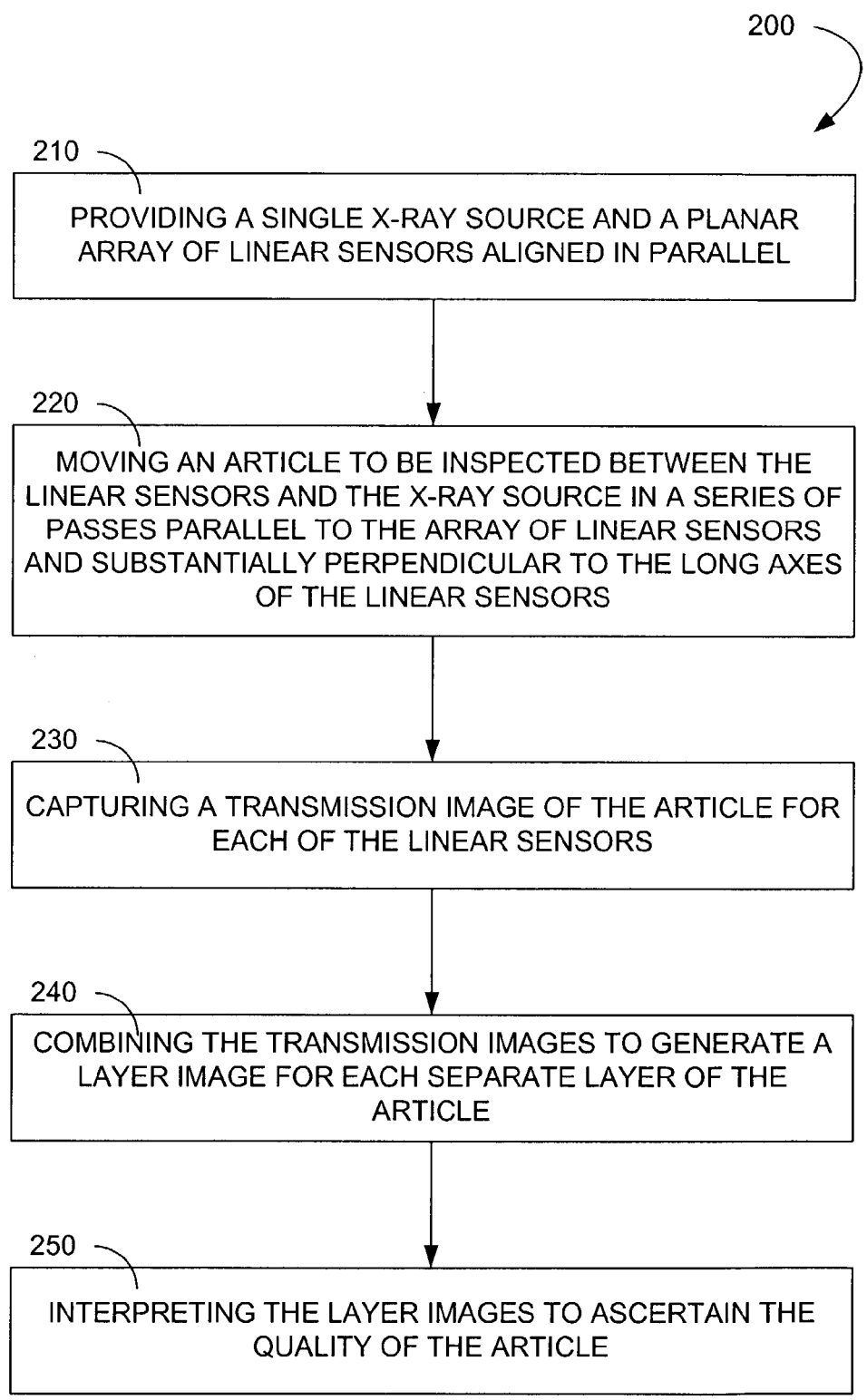
FIG. 5 is a flow diagram of an x-ray inspection method according to an embodiment of the invention.

As shown in FIG. 5, alternate embodiments of the present invention include a method 200 for inspecting articles by way of x-rays. First, a single x-ray source and a planar array of linear sensors are provided, with the sensors aligned in parallel with each other (step 210). Next, an article under inspection is moved between the linear sensors and the x-ray source in a series of passes parallel to the array and substantially perpendicular to the long axis of each linear sensor (step 220). Alternately, the x-ray source and the linear sensors are moved as a unit in relation to a stationary article in a similar fashion (step 220). During the series of passes made by the article relative to the linear sensors, a transmission image of the article is captured for each of the sensors in the array (step 230). The transmission images are combined mathematically to generate a layer image for each separate conceptual "layer" of the is article (step 240). The generated layer images may then be interpreted to ascertain the physical quality of the article for inspection purposes (step 250).

From the foregoing, embodiments of the invention involve an improved system and method for physical x-ray inspection of an article which provide high-quality multi-layer x-ray imaging utilizing multiple linear sensors in a system of comparatively low cost and complexity. Embodiments of the invention other than those shown above are also possible. As a result, the invention is not to be limited to the specific forms so described and illustrated; the invention is limited only by the claims.

What is claimed is:

1. An x-ray inspection system, comprising:
    an imaging chain, comprising a single x-ray source and a planar array of linear sensors, the long axes of the linear sensors being aligned in parallel, the linear sensors being configured to receive x-rays from the x-ray source, the x-ray source and the linear sensors remaining stationary with respect to each other;
    a relative motion mechanism configured to alter the position of an article to be inspected relative to the imaging chain by passing the article between the x-ray source and the array of linear sensors in a series of passes, parallel to the array of linear sensors and substantially perpendicular to the long axes of the linear sensors, each pass displaced from the prior pass in a direction along the long axes of the sensors;
    an interpreter configured to capture a transmission image of the article for each of the linear sensors and combine the transmission images in order to generate a layer image for each separate layer of the article; and
    a controller configured to coordinate and control the relative motion mechanism, the imaging chain, and the interpreter.

2. The system of claim 1, wherein the interpreter is also configured to interpret the layer images to ascertain the quality of the article.

3. The system of claim 1, wherein the relative motion mechanism moves the article under inspection.

4. The system of claim 1, wherein the relative motion mechanism moves the imaging chain as a unit.

5. The system of claim 1, wherein there are between 12 and 16 linear sensors.

6. The system of claim 1, wherein the linear sensors are arranged substantially in a circle.

7. The system of claim 1, wherein the linear sensors are time delay integration (TDI) linear sensors.

8. The system of claim 1, wherein the relative motion mechanism is also configured to alter the position of the article relative to the array of linear sensors in a direction perpendicular to the array of linear sensors to allow modification of the resolution of the transmission images.

9. An imaging chain for an x-ray inspection system, comprising:
    a single x-ray source; and
    a planar array of linear sensors arranged substantially in a circle, the long axes of the linear sensors being aligned in parallel, the linear sensors being configured to receive x-rays from the x-ray source, the x-ray source and the linear sensors remaining stationary with respect to each other.

10. The imaging chain of claim 9, wherein there are between 12 and 16 linear sensors.

11. The imaging chain of claim 9, wherein the linear sensors are time delay integration (TDI) linear sensors.

12. An x-ray inspection system, comprising:
    an imaging chain, comprising a single x-ray source and a planar array of linear sensors, the long axes of the linear sensors being aligned in parallel, the linear sensors being configured to receive x-rays from the x-ray source, the x-ray source and the linear sensors remaining stationary with respect to each other;
    means for altering the position of an article to be inspected relative to the imaging chain by passing the article between the x-ray source and the array of linear sensors in a series of passes, parallel to the array of linear sensors and substantially perpendicular to the long axes of the linear sensors, each pass displaced from the prior pass in a direction along the long axes of the sensors;

means for capturing a transmission image of the article for each of the linear sensors; and means for combining the transmission images in order to generate a layer image for each separate layer of the article.

13. The system of claim 12, further comprising means for interpreting the layer images to ascertain the quality of the article.

14. The system of claim 12, wherein the position altering means moves the article under inspection.

15. The system of claim 12, wherein the position altering means moves the imaging chain as a unit.

16. The system of claim 12, wherein there are between 12 and 16 linear sensors.

17. The system of claim 12, wherein the linear sensors are arranged substantially in a circle.

18. The system of claim 12, wherein the linear sensors are time delay integration (TDI) linear sensors.

19. The system of claim 12, wherein the position altering means also alters the position of the article relative to the array of linear sensors in a direction perpendicular to the array of linear sensors to allow modification of the resolution of the transmission images.

20. A method for inspecting an article by the use of x-rays, comprising:

providing a single x-ray source and a planar array of linear sensors, the long axes of the linear sensors being aligned in parallel, the linear sensors being configured to receive x-rays from the x-ray source, the x-ray source and the linear sensors remaining stationary with respect to each other;

altering the position of an article to be inspected relative to the x-ray source and the array of linear sensors by passing the article between the x-ray source and the array of linear sensors in a series of passes parallel to the array of linear sensors and substantially perpendicular to the long axes of the linear sensors, each pass displaced from the prior pass in a direction along the long axes of the sensors;

capturing a transmission image of the article for each of the linear sensors; and combining the transmission images and generating a layer image for each separate layer of the article.

21. The method of claim 20, further comprising interpreting the layer images to ascertain the quality of the article.

22. The method of claim 20, wherein the position altering step moves the article under inspection.

23. The method of claim 20, wherein the position altering step moves the x-ray source and the planar array of linear sensors as a unit.

24. The method of claim 20, wherein there are between 12 and 16 linear sensors.

25. The method of claim 20, wherein the linear sensors are arranged substantially in a circle.

26. The method of claim 20, wherein the linear sensors are time delay integration (TDI) linear sensors.

27. The method of claim 20, further comprising altering the position of the article relative to the array of linear sensors in a direction perpendicular to the array of linear sensors to allow modification of the resolution of the transmission images.

* * * * *